(12) United States Patent
Benner et al.

(10) Patent No.: US 10,415,088 B1
(45) Date of Patent: *Sep. 17, 2019

(54) IN VIVO CONVERSION OF NUCLEOSIDES IN PLASMID DNA

(71) Applicants: Steven A Benner, Gainesville, FL (US); Zunyi Yang, Gainesville, FL (US)

(72) Inventors: Steven A Benner, Gainesville, FL (US); Zunyi Yang, Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/997,325

(22) Filed: Jun. 4, 2018

Related U.S. Application Data

(63) Continuation-in-part of application No. 14/218,405, filed on Mar. 18, 2014, now Pat. No. 9,988,659, which is a continuation of application No. 12/653,613, filed on Dec. 16, 2009, now Pat. No. 9,334,534.

(60) Provisional application No. 61/802,913, filed on Mar. 18, 2013.

(51) Int. Cl.
| | |
|---|---|
| *C12Q 1/68* | (2018.01) |
| *C12Q 1/6869* | (2018.01) |
| *C12P 19/34* | (2006.01) |
| *C12Q 1/6844* | (2018.01) |
| *C07H 21/04* | (2006.01) |

(52) U.S. Cl.
CPC .......... *C12Q 1/6869* (2013.01); *C07H 21/04* (2013.01); *C12P 19/34* (2013.01); *C12Q 1/6844* (2013.01); *C12Q 2521/101* (2013.01); *C12Q 2525/117* (2013.01)

(58) Field of Classification Search
CPC .................................................. C12Q 1/6869
USPC ......................................................... 435/6.1
See application file for complete search history.

(56) References Cited

U.S. PATENT DOCUMENTS 8,614,072 B2 * 12/2013 Benner ................. C12Q 1/686
435/6.1
9,334,534 B1 5/2016 Benner

OTHER PUBLICATIONS

Brownie J. 1997 The elimination of primer-dimer accumulation in PCR. Nucleic Acids Res. 25, 3235-3241.
Elbeik T. 2004 Simultaneous runs of the Bayer VERSANT HIV-1 version 3.0 and HCV bDNA version 3.0 quantitative assays on the system 340 platform provide reliable quantitation and improved work flow. J. Clin. Microbiol., 42, 3120-3127.
Elbeik T. 2004 Mulicenter evaluation of the performance charateristics of the Bayer VERSANT HCV RNA 3.0 assay (bDNA). J. Clin Microbiol., 42, 563-569.
Horlacher J. 1995 Recognition by viral and cellular DNA polymerases of nucleosides bearing bases with non-standard hydrogen bonding patterns. Proc. Natl. Acad. Sci., 6329-6333.
Hutter D 2003 ) Expanding the genetic alphabet. Non-epimerizing nucleoside with the pyDDA hydrogen bonding pattern. J. Org. Chem., 68, 9839-9842.
Johnson S C 2004 A third base pair for the polymerase chain reaction: inserting isoC and isoG. Nucleic Acids Res. 32, 1937-1941.
Jurczyk S C 2000 Synthesis and characterization of oligonucleotides containing 2'-deoxyxanthosine using phosphoramidite chemistry. Helv. Chim. Acta 83, 1517-1524.
Jurczyk S C 1998 Sythesis of oligonucleotides containing 2'-deoxyisoguanosine and 2'-deoxy-5-methyliso-cytidine using phosphoramidite chesmistry. Helv. Chim. Acta 81, 793-811.
Jurczyk S C 1999 Synthesis of 2'-deoxyisoguanosine triphosphate and 2'-deoxy-5-methyl-isocytidine triphoshate. Helv. Chim. Acta. 82, 1005-1015.
Kim H-J 2009 2'Deoxy-1-methylpseudocytidine, a stable analog of 2'-deoxy-5-methylisocytidine. Bioorg Med. Chem. 17, 3728-373.
Kodra J 1997 Sythesis of an N-alkyl derivative of 2'deoxyisoguanosine. Syn. Lett., 939-940.
Lutz S 1999 An in vitro screening technique for polymerases that can incorporate modified nucleotides. Pseudouridine as a substrate for thermostable polymerases. Nucl. Acids Res. 27. 2792-2798.
Martinot T A 2004 Expanding the genetic alphabet: 7-Deaza-isoguanosine favors the 1N-H keto form by 103-to-1 over the enol. J. Org. Chem. 69, 3972-3975.
Murakami K 1991 *Escherichia coli* mediated biosynthesis and in vitro Anti-HIV Activity of lipophilic 6-Halo-2'.3'-dideoxpurine nucleosides. J. Med. Chem. 34, 1606-1612.
Piccirilli J A 1990 Extending the genetic alphabet. Enzymatic incorporation of a new base pair into DNA and RNA Nature 343, 33-37.
Piccirilli J A 1991 A direct route to 3-(ribofuranosyl)-pyridine nucleosides. Helv. Chim. Acta 74, 397-406.
Sepiol J 1976 Tautomerism of iso-guanosine and solvent-induced keto-enol equilibrum. Z. Naturforsch 31C, 361-370.
Sismour A M 2005 The use of thymidine analogs to improve the replication of an extra DNA base pair: A synthetic biological system. Nucl. Acids Res. 33, 5640-5646.
Switzer C Y 1989 Enzymatic incorporation of a new base pair into DNA and RNA. J. Am. Chem. Soc. 111, 8322-8323.
Switzer C Y 1993 Enzymatic recognition of the base pair between iso-cytidine and iso-guanosine. Biochemistry 32, 10489-10496.
Tang Y 2006 Synthesis and biological evaluation of carboacyclic nucleosides with (Z) and (E)-9-[4,4-bis(hydroxymethyl)]-2-butenyl side chain. Bioorg. Med Chem. Lett. 14, 5866-5875.

(Continued)

*Primary Examiner* — Jezia Riley

(57) ABSTRACT

Disclosed are processes that use DNA polymerases to extend primers annealed to templates, wherein a standard nucleotide in the template guiding the extension directs the incorporation of a nonstandard nucleotide analog into the product duplex opposite that standard template nucleotide, and processes wherein a nonstandard nucleotide in the template guiding the extension directs the incorporation of a standard nucleotide analog opposite the nonstandard template nucleotide. Conditions, including the pH of the mixture where the primer extension is done and the composition of triphosphate mixtures where the primary extensions done, are disclosed.

14 Claims, 10 Drawing Sheets

Figure 1:
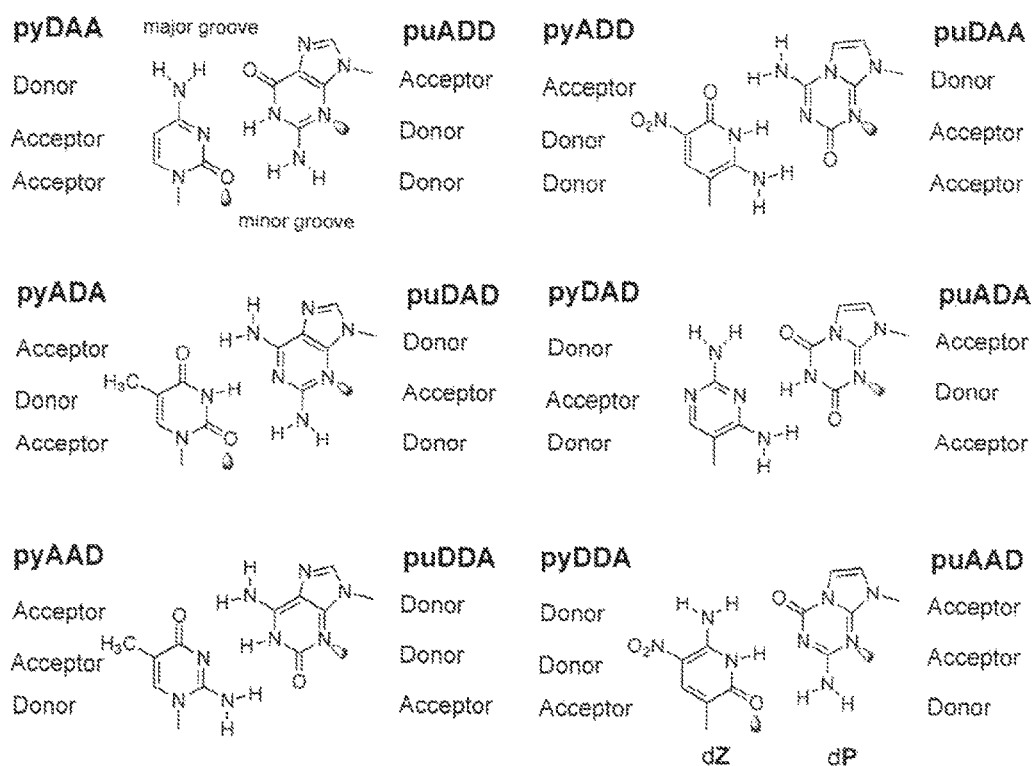

Specification includes a Sequence Listing.

(56) References Cited

OTHER PUBLICATIONS

Voegel J J 1993 Synthesis and tautomeric equilibrium of 6-amino-5-benzyl-3-methylpyrazin-2-one. An acceptor-donor-donor nucleoside base analog. J. Org. Chem. 58, 7542-7547.

Voegel J J 1996 Synthesis and characterization of non-standard nucleosides and nucleotides bearing the acceptor-donor-donor pyrimidine analog 6-amino-3-methylpyrazin-2-one. Helv. Chim. Acta 79, 1863-1880.

Voegel JJ 1996 Synthesis, molecular recognition & enzymology of oligunucleotides containing the non-standard base pair between 5-aza-7-deaza-iso-guanine & 6-amino-3-methylpyrazin-2-one, a donor-acceptor-acceptor purine analog and an acceptor-donor-donor pyrimidine analog. Helv. Chim. Acta 79, 1881-1898.

Von Krosigk U 1995 pH-independent triple helix formation by an oligonucleotide containing a pyrazine donor-donor-acceptor base. J. Am. Chem. Soc. 117, 5361-5362.

Yang Z 2006 Artificially expanded genetic information system. A new base pair with an alternative hydrogen bonding pattern. Nucleic Acids Res., 34, 6095-6101.

Yang Z 2007 Enzymatic incorporation of a third nucleobase pair. Nucl Acids Res. 35, 4238-4249.

\* cited by examiner ns US 10,415,088 B1

IN VIVO CONVERSION OF NUCLEOSIDES IN PLASMID DNA

CROSS REFERENCE TO RELATED APPLICATIONS

This application is a continuation-in-part of U.S. patent application Ser. No. 14/218,405, currently pending, entitled "In Vivo Conversion of Nucleosides Plasmid DNA". U.S. patent application Ser. No. 14/218,405 was a continuation-in-part on U.S. patent application Ser. No. 12/653,613, filed Dec. 16, 2009, entitled "Processes replacing standard nucleotides by non-standard nucleotides and non-standard nucleotides by standard nucleotides in DNA, now issued as U.S. Pat. No. 9,334,534. U.S. patent application Ser. No. 14/218,405 claims priority to U.S. provisional patent application 61/802,913, entitled "In vivo Conversion of Nucleosides in Plasmid DNA", which was filed Mar. 18, 2013.

STATEMENT OF RIGHTS TO INVENTIONS MADE UNDER FEDERALLY-SPONSORED RESEARCH

None.

THE NAMES OF THE PARTIES TO A JOINT RESEARCH AGREEMENT

Not applicable.

INCORPORATION-BY-REFERENCE OF MATERIAL SUBMITTED ON A COMPACT DISC

None

BACKGROUND OF THE INVENTION (1) Field of the Invention

The field of this invention is nucleic acids and their analogs, more specifically nucleotide analogs that can form non-standard Watson-Crick nucleobase pairs that have similar geometry as standard Watson-Crick pairs, but are joined by a not hydrogen bonding schemes. More specifically, this invention relates to processes that introduce these analogs into oligonucleotides via enzymatic processes that mismatch non-standard nucleotides against standard nucleotides to create orthogonally capturable tags. This invention further relates to processes and pairs of processes that replace non-standard nucleotides by more than one standard nucleotides, leading to clonable products and, in particular, to two clonable products whose sequences, when compared, allow the inference of the sites in the original oligonucleotide sequence where non-standard nucleotides were present.

(2) Description of Related Art

Natural oligonucleotides bind to complementary oligonucleotides according to Watson and Crick rules of nucleobase pairing, where adenine (A) (or 2-aminoadenine) pairs with thymine (T) (or uracil, U), and guanine (G) pairs with cytosine (C), with complementary strands anti-parallel to one another. In this disclosure, "DNA" or "nucleic acid" is understood to include, as appropriate, both DNA (where the sugar is 2'-deoxyribose) and RNA (where the sugar is ribose), the 2'-O-alkyl and allyl derivatives, and these nucleic acids and their analogs in non-linear topologies, including dendrimers, comb-structures, and nanostructures, and these nucleic acids and their analogs carrying tags (e.g., fluorescent, functionalized, or binding) to the ends, sugars, or nucleobases, and/or non-nucleotidic material attached to the ends of the strand.

These pairing rules, which are largely context tree and which can be applied without undue experimentation even by high school students, allow specific hybridization of an oligonucleotide to a complementary oligonucleotide, making oligonucleotides valuable as probes in the laboratory, in diagnostics, as messages that can direct the synthesis of specific proteins, and in other applications well known in the art. Such base pairing is used, as an example and without limitation, to capture other oligonucleotides to beads, arrays, and other solid supports, in linear and dendrimeric structures, to allow nucleic acids to fold in hairpins, beacons, and catalysts, as supports for functionality, such as fluorescence, fluorescence quenching, binding/capture tags, and catalytic functionality, as part of mote complex architectures, including dendrimers and nanostructures, and as scaffolds to guide chemical reactions.

Further, nucleobase pairing is used by enzymes to catalyze the synthesis of new oligonucleotides that are complementary to template nucleotides. In this synthesis, building blocks (normally the triphosphates of ribo- deoxyribonucleosides carrying of A, T, U, C, or G) are directed by a template oligonucleotide to form a complementary oligonucleotide with the complementary sequence. This serves as the basis for technologies for enzymatic synthesis and amplification of specific nucleic acids by enzymes such as DNA and RNA polymerase, in the polymerase chain reaction (PCR), and in a variety of architectures that may involve synthesis, ligation, cleavage, immobilization and release, inter alia, used in technology to detect nucleic acids.

The Watson-Crick pairing rules can be understood chemically as a consequence of the arrangement of hydrogen bonding groups on the heterocyclic nucleobases of the oligonucleotide, groups that can either be hydrogen bond donors or acceptors. In the standard Watson-Crick geometry, a large purine nucleobase pairs with a small pyrimidine nucleobase. Thus, the AT nucleobase pair is the same size as a GC nucleobase pair; the rungs of the DNA ladder, formed from either AT or GC nucleobase pairs, all have the same length. In this disclosure, to be "complementary in the Watson-Crick sense" means to have the Watson-Crick geometry, a full pairing (not wobble pairing) of a large purine and a small pyrimidine held together by three hydrogen bonds, or (if context demands) two hydrogen bonds, where in pairing is said to be "against" the nucleotide in the complementary strand, in an antiparallel orientation, to which it is matched.

The specificity of recognition between large and small nucleobases is determined by hydrogen bonding between the nucleobases. In standard nucleobases, hydrogen bond donors are heteroatoms (nitrogen or oxygen in the natural nucleobases) bearing a hydrogen, while hydrogen bond acceptors are heteroatoms (nitrogen or oxygen in the natural nucleobases) with a lone pair of electrons. In the Watson-Crick nucleobase pairing geometry, a six membered ring (in standard nucleobases, a pyrimidine) pairs with a ring system composed of a fused five-six ring system (in standard nucleobases, a purine), with a middle hydrogen bond linking two ring atoms, and hydrogen bonds on either side functional groups appended to each of the rings, with donor groups paired with acceptor groups. The AT nucleobase pair uses this hydrogen bonding pattern only partly; it is completely used in the diaminoA:T base pair.

In 1990, the instant Inventor filed the first patent application (which later issued as U.S. Pat. No. 5,432,272)

disclosing compositions of matter that expanded the number of nucleobases that could pair by such simple rules. He proposed eight additional nucleobases that form four additional pairs by changing the pattern of hydrogen bond donor and acceptor groups presented by a nucleobase to the nucleobase on a complementary oligonucleotide analog [U.S. Pat. Nos. 5,432,272, 5,965,364, 6,001,983, 6,037,120, 6,140,496, 6,627,456, 6,617,106]. These disclosures showed that the geometry of the Watson-Crick nucleobase pair could accommodate as many as 12 nucleobases forming 6 mutually exclusive pairs. Of these, four nucleobases forming two pairs are "standard", while eight nucleobases forming four pairs were termed "non-standard". Adding the non-standard nucleobases to the standard nucleobases yielded an Artificially Expanded Genetic Information System (AEGIS). It was also noted that these nucleobases analogs might be functionalized to enable a single biopolymer capable of both genetics and catalysis.

Expanded genetic alphabets have now been explored in many laboratories, and the possibility of a fully artificial genetic system has been advanced [Swi89][Pic90][Pic91] [Voe93][von95][Voe96a][Voe96b][Kod97][Jur98][Lut99] [Jur99][Jur00], the contents of which are incorporated by reference.

To systematize the nomenclature for the hydrogen bonding patterns, the hydrogen bonding pattern implemented on a small component of a nucleobase pair are designated. by the prefix "py". Following this prefix is the order, from the major groove to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Again following the prefix, the hydrogen bond donor and acceptor groups are designated, from the major or to the minor grooves, using "A" and "D". Thus, standard nucleobases adenine and guanine implement the standard hydrogen bonding patterns puDA~ and puADD respectively.

A teaching of this disclosure that hydrogen-bonding patterns designated using this systematic nomenclature are distinct in concept from the organic molecules that are used to implement the hydrogen-bonding patterns. Thus, guanosine is a nucleotide that implements the puADD hydrogen-bonding pattern. So does, however, 7-deazaguanosine, 3-deazaguanosine, 3,7-dideazaguanosine, and any of any number of other purines and purine derivatives, including those that carry side chains to which are appended functional groups, such as fluorescent, fluorescent quencher, attachment, or metal complexing groups. Which organic molecule is chosen to implement a specific hydrogen-bonding pattern determines, in large part, the utility of the non-standard hydrogen-bonding pattern, in various applications to which it might be applied.

The additional nucleobase pairs, because of their desirable pairing properties, chemical stability, and other features known to those skilled in the art, have been useful for a variety of purposes. For example, the nucleobase pair between 2-amino-5-methyl-1-(1'-beta-D-2'-deoxyribofuranosyl)-4(1H)-pyrimidine, also known as 2'-deoxyisocytidine, disoC, or sometimes (less correctly) isoC and implementing the pyAAD hydrogen bonding pattern, and 6-amino-1,9-dihydro-9-(1'-beta-D-2'-deoxyribofuranosyl)-3H-purin-2-one, also known as 2'-deoxyisoguanosine, disoG, or sometimes (less correctly) isoG, and implementing the puDDA hydrogen bonding pattern, is incorporated into the branched DNA diagnostics tools that were marketed by Bayer and its successor, Siemens Diagnostics. Here, the non-standard nucleobase pair supports orthogonal molecular recognition in aqueous solution, similar to nucleic acids but with a coding system that is orthogonal to the system in DNA and RNA, Thus, it allows the assembly of the branched dendrimer in the assay free from inhibition by adventitious nucleic acid, and prevents adventitious nucleic acid from capturing signaling elements form the nanostructure in the absence of the target analyte nucleic acid, creating noise. Further, adding extra letters to the genetic alphabet speeds hybridization, presumably because it decreases the number of close mismatches where DNA dwells before finding its fully matched partner. The branched DNA assay has FDA-approval and is widely used to provide personalized patient care in the clinic.

One advantage of incorporating non-standard nucleotides into human diagnostic assays is that binding between oligonucleotides containing these can occur without interference from natural DNA, which is often present in abundance in samples taken from human tissues. Such binding is often used to concentrate samples from complex mixtures, on arrays or at the bottom it plastic wells. Natural DNA, built from A, T, G, and C, will interfere with A:T and G:C interactions. This leads to large amounts of noise in DNA arrays, for example. Accordingly, in the branched DNA assays, non-standard nucleotides are incorporated by chemical synthesis into the portion of tags that are used to move the analyte to a spot where it can be detected and to assemble signaling dendrimers.

Pairing between non-standard nucleotides cannot be used to directly bind natural analytes, as these analytes are themselves built from A, T, G, and C. Accordingly, when non-standard nucleotides are used to achieve orthogonality in clinical diagnostic assays [Elb04a][Elb04b], they are general appended as tags to primary probes, which are built from A, T, G, and C. The primary probes are the ones that contact the analyte targeted by the diagnostic assay. This limits considerably the use of non-standard components to achieve orthogonality and high signal-to-noise ratios in biological systems. A process that creates replicates or complements of oligonucleotides that replace in a controlled fashion standard nucleotides by non-standard nucleotides would therefore have utility. If this is sequence specific, the pairing the resulting replicate or complement through non-standard base pairs could, in an appropriate architecture, offer an element of selectivity for the analyte in addition to those selectivity elements based on other regions of the analyte (for example, the regions that bind PCR amplification primers).

Conversely, oligonucleotides containing non-standard nucleotides cannot today be introduced into standard cloning systems. No strain used for cloning, including *E. coli* strains, is known to have the cellular machinery for making the triphosphates of non-standard nucleosides and using them to replicate DNA containing non-standard nucleotides. A process that creates replicates or complements of oligonucleotides that replace in a controlled fashion non-standard nucleotides by standard nucleotides (a vice versa process) would therefore have utility. Further, such a process would most useful if it is a process pair, where the product from one process replaces the non-standard nucleotide by one standard nucleotide, and another replaces the non-standard nucleotide by a different standard nucleotide. This makes it possible to compare the sequences of the two resulting replicates or complements to ascertain where in the oligonucleotide sequence the original non-standard nucleotide(s) was (were) found.

Mismatching is known between non-standard and standard pairs such that a standard nucleotide is incorporated opposite a nonstandard nucleotide in the template. For example, Sepiol et al. [Sep76] recognized that isoG, which presents a hydrogen bond donor-donor-acceptor pattern complementary to the acceptor-acceptor-donor pattern of isoC, exists in water to about 10% as an enol tautomeric form, which can present a hydrogen bond donor-acceptor-donor hydrogen bonding pattern complementary to T (acceptor-donor-acceptor). Work in the 1990's showed that polymerases of various types would incorporate T (or U) opposite isoG in a template, presumably by pairing between T (or U) and the minor tautomeric form of isoG [Swi93]. This caused the loss of the isoG:isoC pair in (for example) PCR reactions [Joh04], a loss that was considered throughout the art to be disadvantageous, as it appeared to deprive the product from the possibility of the PCR product of having the orthogonal isoC:isoG pair.

Struggling to suppress this mispairing between T and the minor tautomeric form of isoG, the instant Inventor and Michael Sismour exploited the discovery that the minor tautomer of isoG does not pair well with 2-thio, and replaced T with 2-thioT in a polymerase incubation [Sis05]. Therefore, products derived from a six letter PCR incorporating A, G, C, 2-thioT, isoG and isoC was able to retain the isoC and isoG non-standard components after many more cycles than a six letter PCR where standard T was used instead of 2-thioT. Thus, the products were able to retain the ability to be orthogonally bound by isoG:isoC pairing after many more cycles of PCR. Further attempting to avoid mispairing and isoG:T (or U) mismatching, 7-deazaisoG was developed [Mar04].

These examples, from the prior art show the extent to which those in the art view as undesirable the mismatching between standard nucleotides and non-standard nucleotides, and thereby teach away from the instant invention, which is based on an inventive step that recognizes the utility of mismatching.

BRIEF SUMMARY OF THE INVENTION

The processes of invention use DNA polymerases that incorporate non-standard nucleotides or intermediary nucleotides opposite standard nucleotides in a parent temp/ate to produce, after one or more polymerase extension steps, product oligonucleotides that have non-standard nucleotides replacing specific standard nucleotides in the parent. Also disclosed are vice versa processes that produce product oligonucleotides that have standard nucleotides replacing specific non-standard nucleotides in the parent.

BRIEF DESCRIPTION OF THE SEVERAL VIEWS OF THE DRAWING(S)

FIG. 1. One example of an "artificially expanded genetic information system" (AEGIS). Nucleobase pairs in this system have a Watson-Crick geometry, with large purines or purine analogs (indicated by "pu") pairing with small pyrimidines or pyrimidine analogs (indicated by "py") joined by hydrogen bonds. The hydrogen-bonding acceptor (A) and donor (D) groups are listed from the major to the minor groove as indicated. The heterocycles shown are the currently preferred implementations of the indicated hydrogen bonding patterns; others are conceivable. Electron density presented to the minor groove is shown by the shaded lobes. Note that some non-standard pyrimidines do not present this density. The nucleotides implementing the pyDDA:puAAD hydrogen bonding pattern, the topic of this paper, are at the bottom right.

Figure 2:
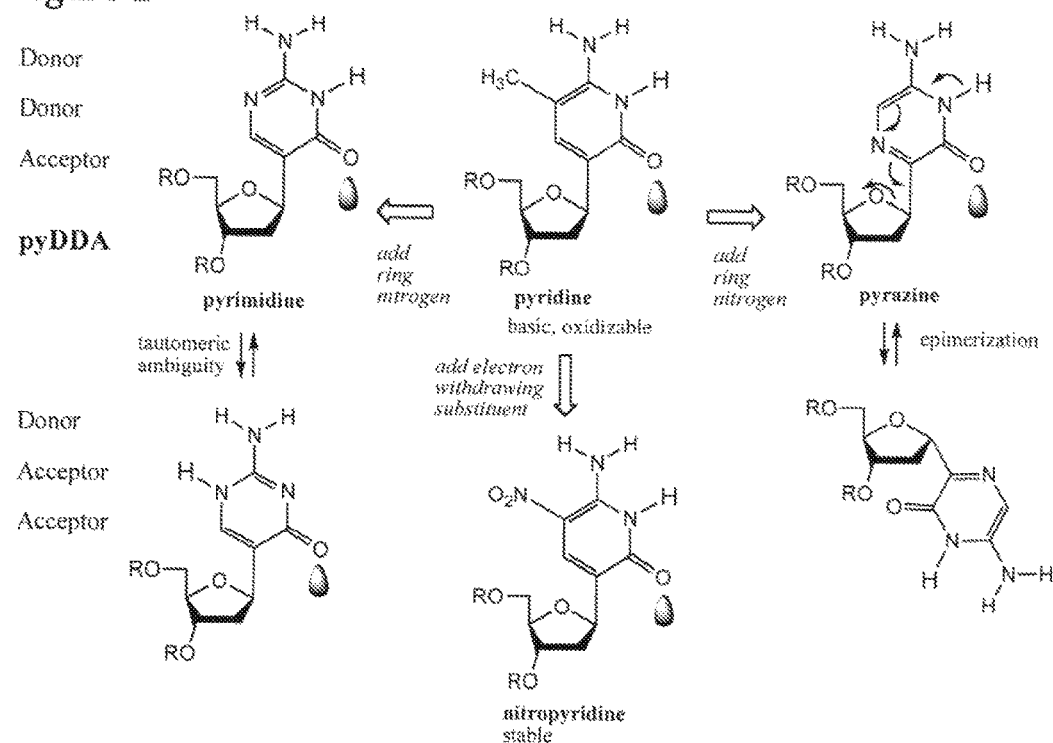

FIG. 2. Four alternative implementations of the pyDDA hydrogen bonding pattern. The implementation on a pyrimidine heterocycle suffers from tautomeric ambiguity (left). The implementation on a pyrazine suffers from facile epimerization (right). The implementation on a simple pyridine is too basic and prone to oxidation (top center). The preferred implementation is the nitropyridine heterocycle (discussed here, bottom center), which is stable to oxidation, is not basic, and does not epimerize near neutral pH.

Figure 3:
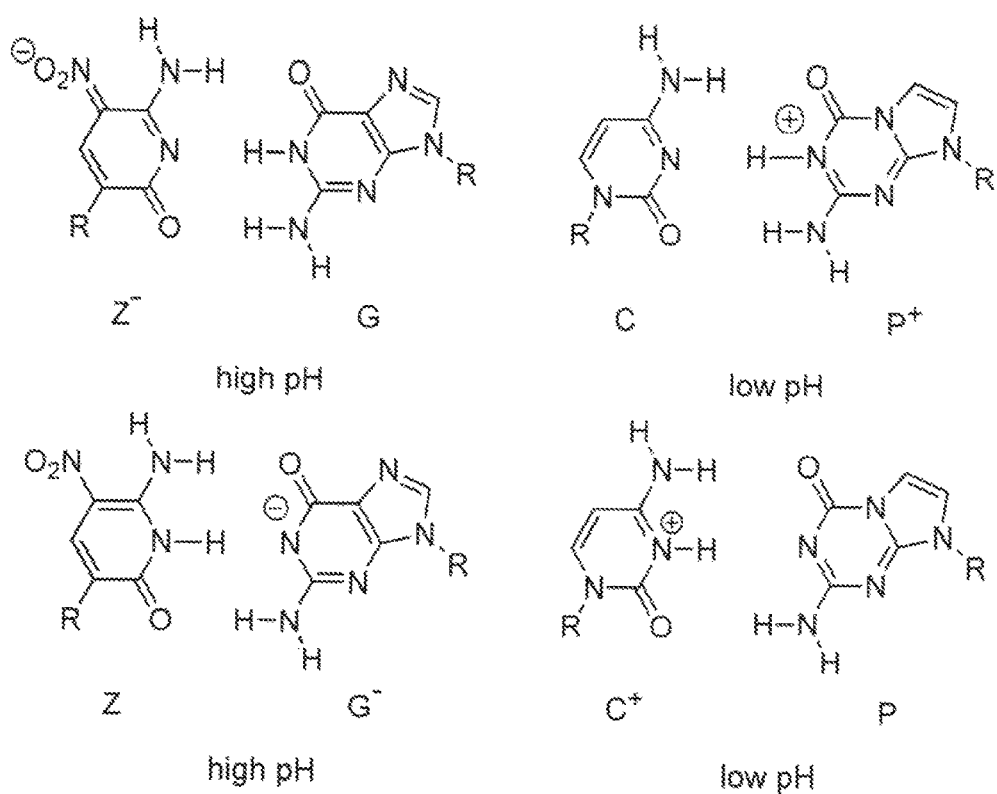

FIG. 3. Nucleobases structured to place non-standard nucleotides in a polymerase-generated product opposite specific standard nucleotides using protonated and deprotonated formula. The R is the point of attachment to the DNA backbone.

Figure 4:
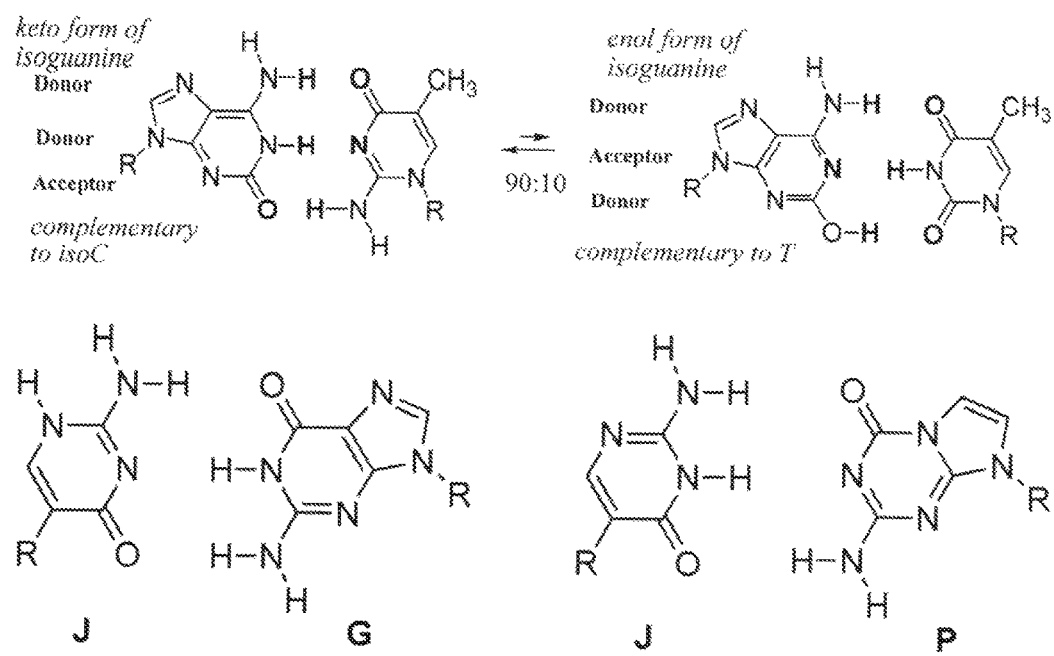

FIG. 4. Nucleobases structured to place non-standard nucleotides in a polymerase-generated product opposite specific standard nucleotides by virtue of their having tautomeric forms.

Figure 5:
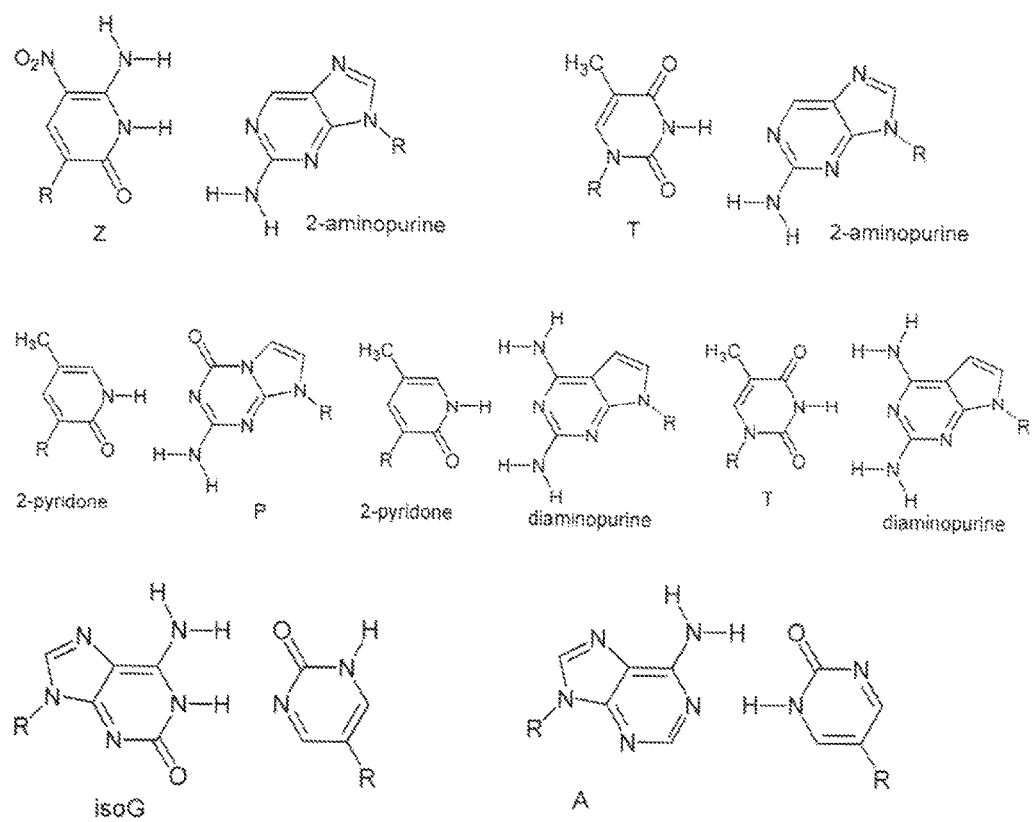

FIG. 5. Nucleobases structured to place non-standard nucleotides in a polymerase-generated product opposite specific standard nucleotides exploiting a nucleobase that presents two hydrogen bond that a standard and non-standard base have in common.

Figure 6:
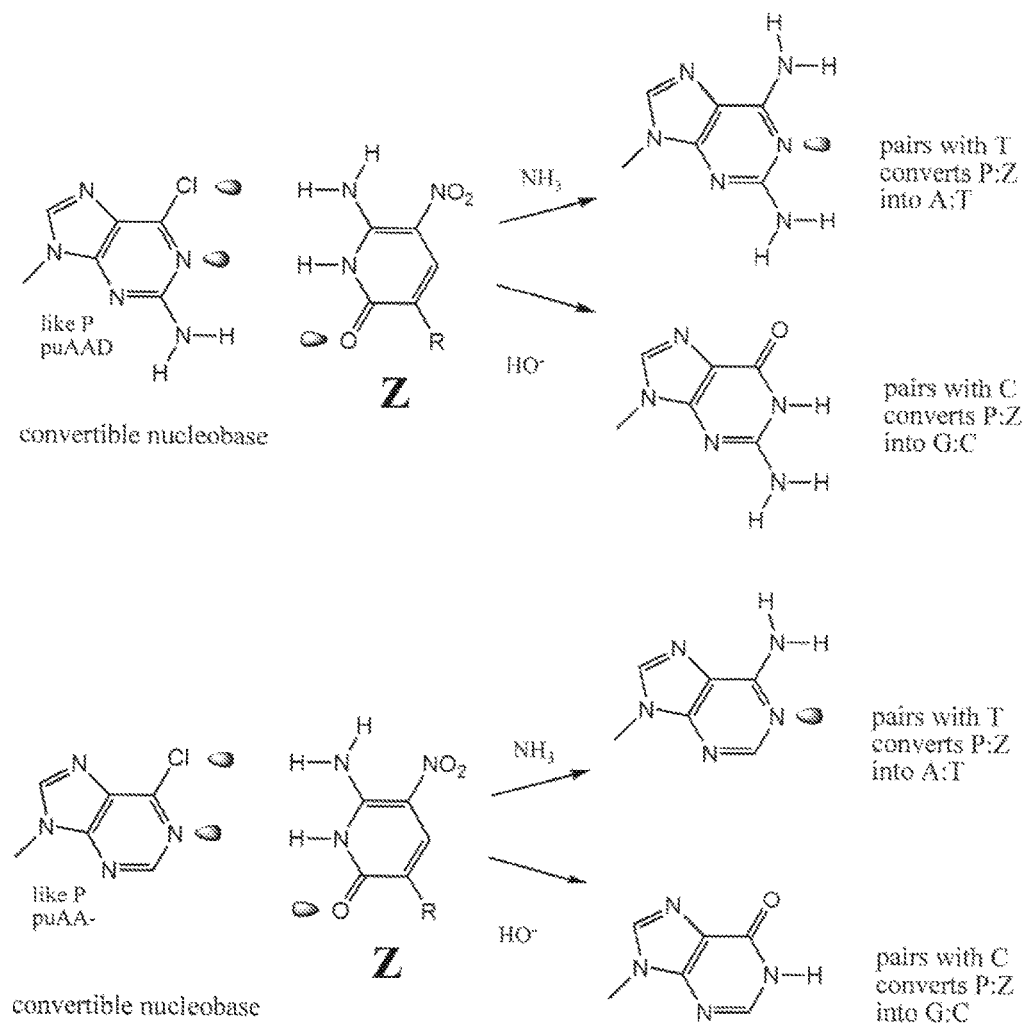

FIG. 6. Nucleobases structured to place standard nucleotides polymerase-generated product opposite specific non-standard nucleotides exploiting a nucleobase that complements the non-standard base that, upon subsequent treatment with chemical reagents, can generate two different standard nucleobases. This allows the products to be cloned, and further allows one to compare the sequences in the cloned products to decide where the non-standard nucleotides originally were.

Figure 7:
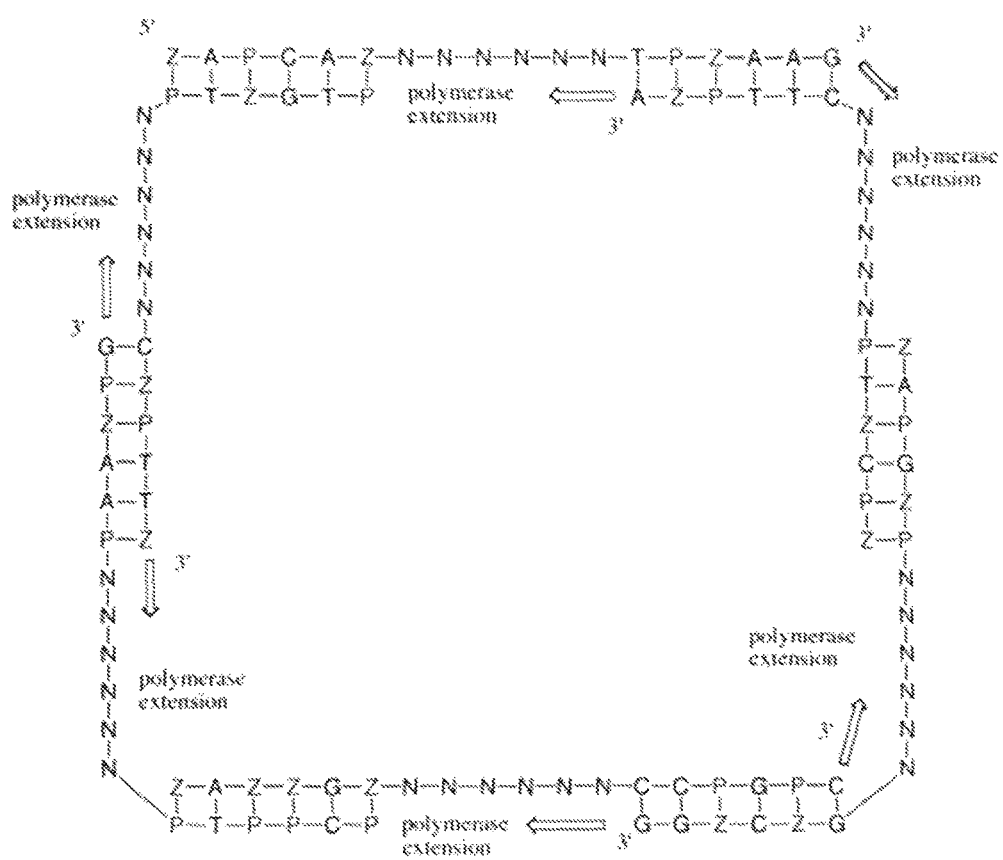

FIG. 7. Schematic showing the first step of the strategy for creating a circular DNA construct using the method of the instant invention.

Figure 8:
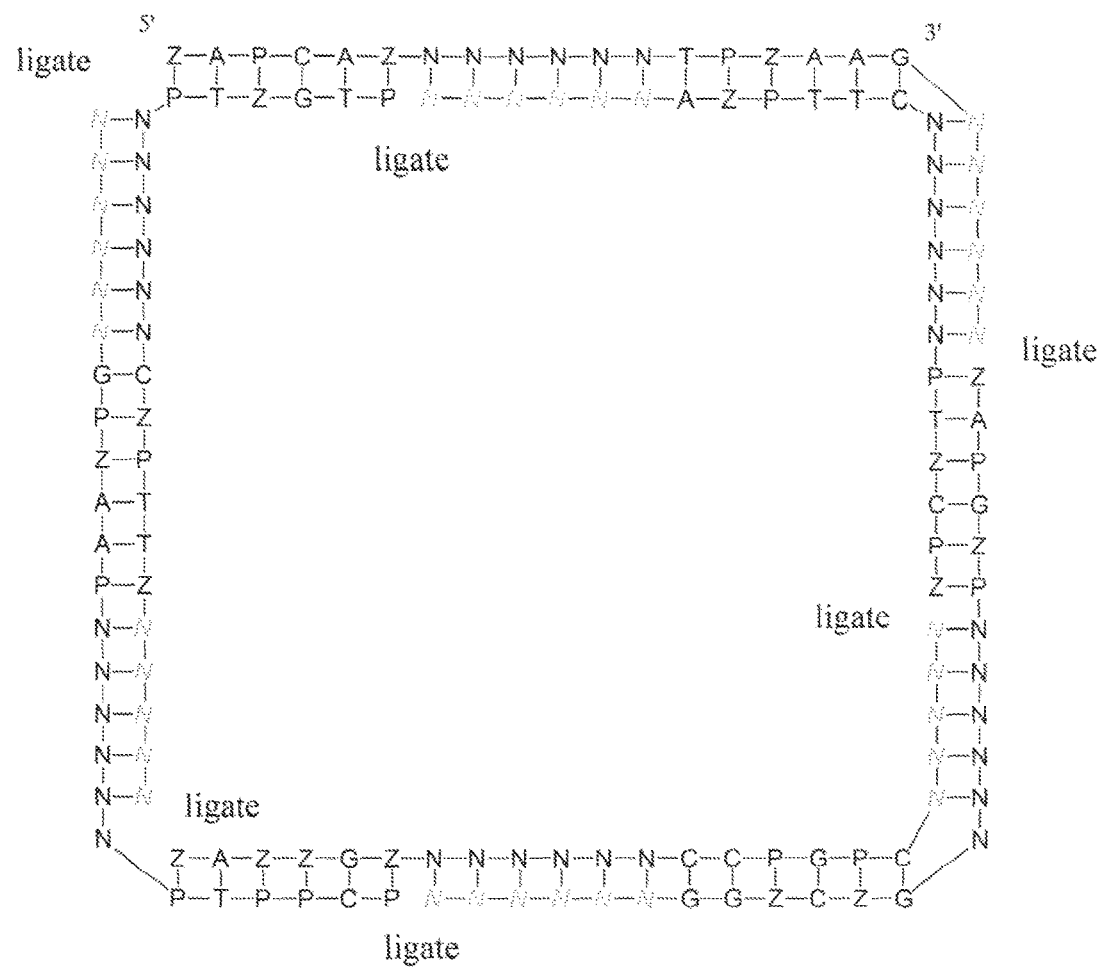

FIG. 8. Schematic showing the second step of the strategy for creating a circular DNA construct using the method of the instant invention.

Figure 9:
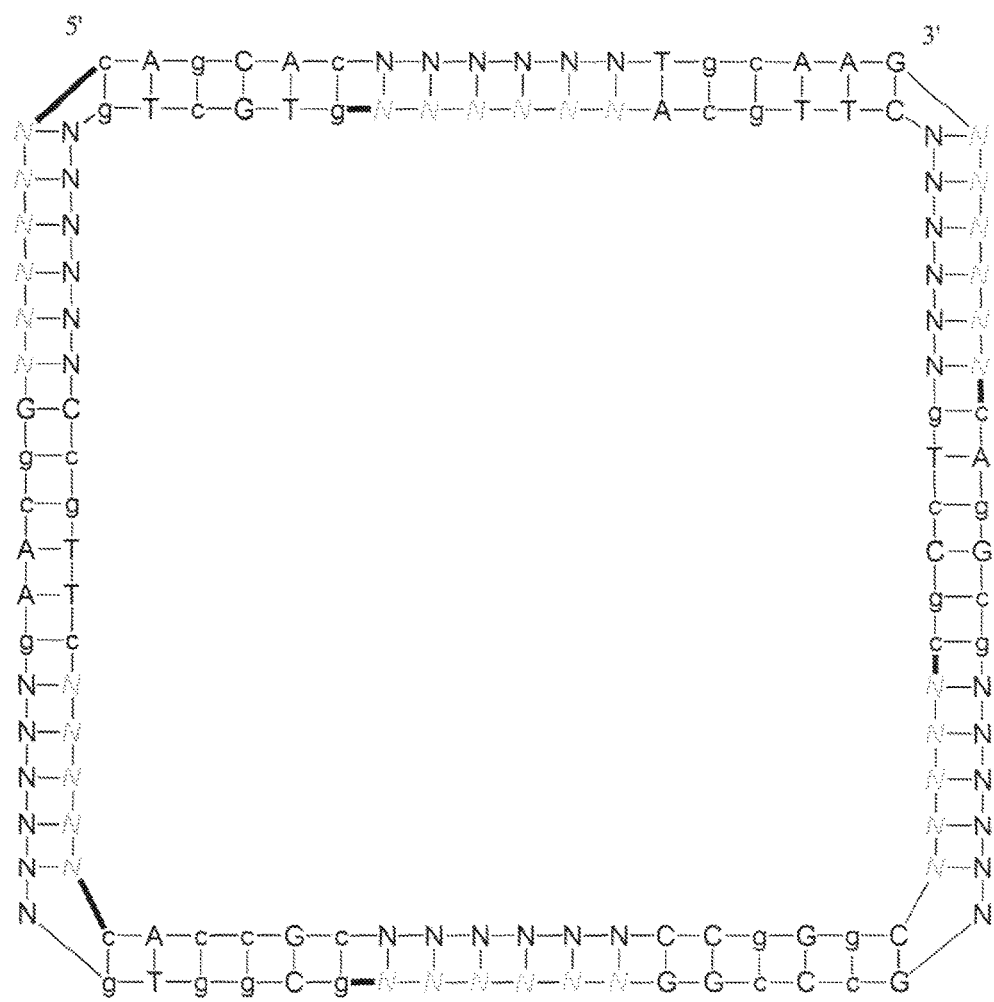

FIG. 9. Schematic showing the third step of the strategy or creating a circular construct using the method of the instant invention.

Figure 10:
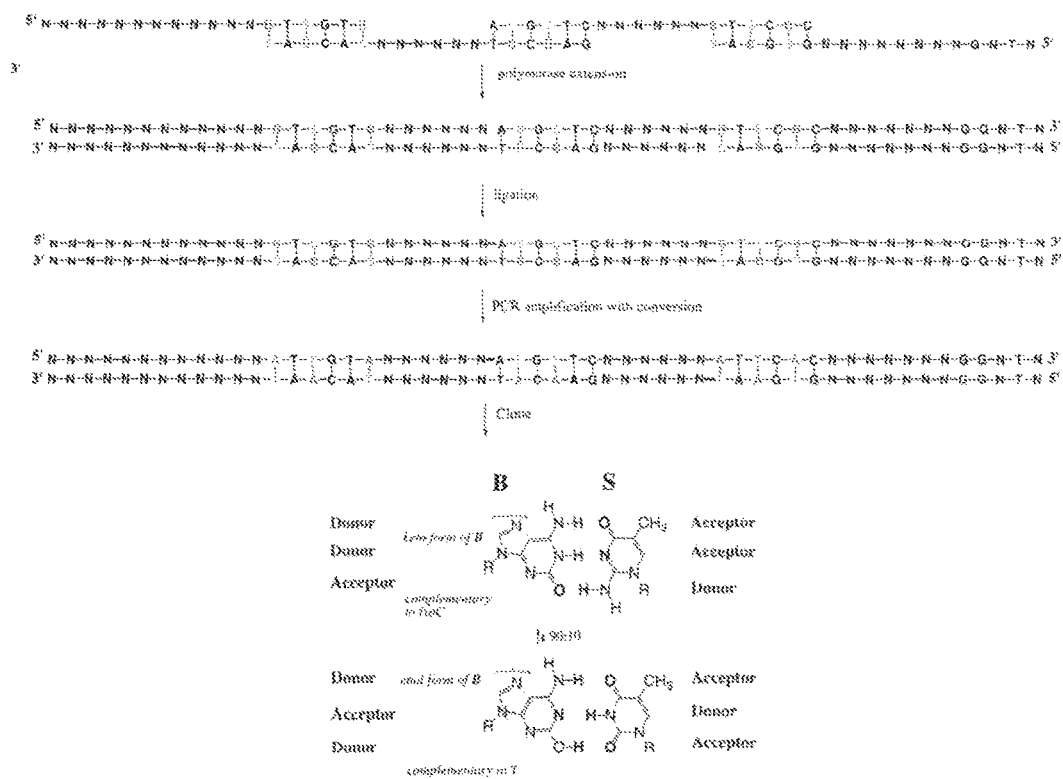

FIG. 10. Schematic showing the details of the transliteration in DNA construct using the method of the instant invention.

DETAILED DESCRIPTION OF THE INVENTION

This application is a continuation-in-part of U.S. patent application Ser. No. 14/218,405, currently pending, entitled "In Vivo Conversion of Nucleosides to Plasmid DNA". The disclosure, examples, and figures of U.S. patent application Ser. No. 14/218,405 are incorporated herein in their entirety by reference. U.S. patent application Ser. No. 14/218,405 was a continuation-in-part of U.S. patent application Ser. No. 12/653,613 entitled "Processes replacing standard nucleotides by non-standard nucleotides and non-standard nucleotides by standard nucleotides in DNA, now issued as U.S. Pat. No. 9,334,534. The disclosure, examples, and figures of U.S. patent application Ser. No. 12/653,613 are incorporated herein in thein entirety by reference.

The instant invention provides processes that introduce non-standard nucleobases not as tags, but within the oligonucleotide product that is semi-complementary to the original nucleotide. In the sense where it is used here, a semi-complementary oligonucleotide is an oligonucleotide that is fully complementary in the Watson-Crick sense to a reference standard oligonucleotide except at sites where standard nucleotides are mismatched with non-standard nucleotides. In the sense where it is used here, a semi-identical oligonucleotide is an oligonucleotide that is fully identical to a reference standard oligonucleotide except at sites where standard nucleotides are replaced by non-standard nucleotides. It is taught that a semi-identical oligonucleotide can be prepared from a semi-complementary oligonucleotide by copying the first by a polymerase in a process where non-standard nucleotides are matched with non-standard complements. Practically, the compositions of the instant invention are practically useful when the distance between the first and last semi-complementary pair in the semi-complementary duplex is at least 5 nucleotides, where the intervening nucleotides may be standard or non-standard.

The first inventive step in creating these processes was to set aside the prohibition in the art against mismatching, to recognize that mismatches introduced by polymerase copying might he useful.

The next inventive step recognized polymerases may be involved in processes that end up creating replicates or complements where standard components are replaced by non-standard components with sequence specificity, or where non-standard components are replaced by standard components (the vice versa process is achievable in this way, and in the ways described below). It was recognized that this could be done in two ways. In the first, the non-standard nucleotide is directly incorporated opposite a standard nucleotide. In the second, an intermediary nucleotide, having a structure that is neither standard or, in the sense used here, non-standard, might be incorporated opposite the standard nucleotide to give an intermediary oligonucleotide product, and the intermediary oligonucleotide product can be copied using a polymerase and the appropriate triphosphates to give a final product that contains the canonical non-standard nucleotide(s).

Several ways to achieve such replacement were then recognized as further inventive steps. Consider first the direct incorporation of a non-standard nucleotide opposite a standard nucleotide. The nucleobases can be either bases or acids, and therefore adopt protonated and deprotonated forms, respectively. In these protonated and deprotonated forms, the hydrogen bonding pattern that is presented to the complementary nucleobases is different from in the normal form. For example (FIG. 3), wherein the pyDDA nucleobase implemented as 6-amino-3-(2'-deoxy)-D-ribofuranosyl)-5-nitro-1H-pyridin-2-one (dZ) is complementary to the puAAD nucleobase implemented as 2-amino-1,9-dihydro-5-aza-3,7-dideaza-9-(1'-beta-D-2'-deoxyribofuranosyl)-1H-purin-6-one, also known as 7-amino-9-(1'-beta-D-2'-deoxyribofuranosyl)-imidazo[1,2-c]pyrimidin-5(1H)-one (dP), its deprotonated form is complementary to G (puADD). Likewise, while the puAAD nucleobases is complementary to the pyDDA nucleobase its protonated form is complementary to C (pyDAA).

Conditions can be adjusted to facilitate this. While not wishing to be bound by theory, mismatches between dP and standard nucleotides and mismatches between dZ and standard nucleotides do not arise from minor tautomeric forms of non-standard and standard nucleobases, but rather by their protonation and deprotonation. Specifically, protonation on the puAAD dP heterocycle generates a species that is complementary to C. Conversely, protonation of dC creates a protonated nucleotide that is Watson-Crick complementary to dP. Under this mechanism, low pH favors the dC:dP mismatch. Experimental studies showed that this was the case; dP is incorporated opposite dC at lower pH (FIG. 3).

Likewise, deprotonation of the pyDDA heterocycle generates a species that is complementary to G. Conversely, deprotonation of dG generates a species that is Watson-Crick complementary to dZ. Under this mechanism, high pH favors the dZ mismatch. Experimental studies showed that this was the case; dP is incorporated opposite dC at lower pH (FIG. 3).

Experimental work showed that if the pH is adjusted accordingly, and if a primer extension reaction is performed without dCTP or dGTP respectively, dZ is incorporated opposite template dG and dP incorporated opposite template dC at high and low pHs, respectively. In the example above, the sequence 5'-ATGCTTAC-3' generates a copy having the sequence 5'-GTAAGZAT-3' and 5'-PTAAPCT-3'. A screen of polymerases identified several that would do this efficiently, including incorporating non-standard components consecutively opposite the same standard component presented consecutively in the template.

Thus, if a polymerases is provided with dZTP and no dGTP, then copying a template at an appropriate pH should generate a product where dZ is incorporated opposite dG (where dC would normally be incorporated). Correspondingly, if a polymerase is provided with dPTP and no dCTP, then copying a template at an appropriate pH should generate a product where dP is incorporated opposite dC (where dG would normally be incorporated). These can be captured onto (for example) a Luminex bead or an array with complementary puAAD- or pyDDA-containing capture oligonucleotides (respectively), allowing the full benefit of the orthogonality of an expanded genetic alphabet in that capture process. This produces the replacement single polymerase extension.

This can also be done by direct replacement if the non-standard nucleobase has a minor tautomeric form that is complementary to the standard nucleobase. This can be done through incubations that lacked the standard nucleoside triphosphate complement, or by doing template-directed primer extension under conditions adjusted so as to favor the mismatch. For example, if an analyte is used as a template in a primed polymerase reaction where isoG is presented as a triphosphate without dATP, an oligonucleotide with a defined sequence (for illustration, let us choose an arbitrary sequence that is shorter than one that would be useful, but is sufficiently short as to not require a sequence listing, 5'-ATGCTTAC-3'), one would generate the product 5'-GT(isoG)(isoG)GC(isoG)T-3'. This would be captured on a probe containing the non-standard sequence 5'-A(isoC)GC(isoC)(isoC)AC-3'. Thus, the analyte would lead to a specific orthogonal sequence without the need for a tag.

A second way to achieve a replacement is to use an intermediary nucleobase. For example, that intermediary nucleobase may be structured to have more than one tautomeric form, where in one tautomeric form, the nucleobases is complementary to a standard nucleobases, and is, in its other tautomeric form complementary to a non-standard nucleobases. For example (FIG. 4), the aminopyrimidinone nucleobase labeled J (to indicate the 2'-deoxy-1-methylpseudocytidine implementation) in one of its forms is complementary to dG. In its other tautomeric form, J is complementary to P (see [Kim09], whose content is fully incorporated herein through citation). Thus, if a polymerase provided with dJTP and no dCTP, then copying a template at any pH generates a product where dJ is incorporated opposite dC (where dG would normally be incorporated). The product oligonucleotide might be directly captured by a P-containing oligonucleotide, again allowing the full benefit of the orthogonality of an expanded genetic alphabet in that capture process, again producing the replacement a single polymerase cycle, Alternatively, the J-containing oligonucleotide product may be treated as an intermediary, and copied with dPTP to obtain a replicate of the original oligonucleotide where dG's are replaced by dP's. The vice versa process using dJTP creates, after two polymerase extensions, derived oligonucleotides where the Z:P pairs have been replaced by C:G pairs. Such derived oligonucleotides can be cloned and sequenced using standard methods.

A third approach recognizes that in some cases, a nonstandard nucleobase and a standard nucleobase share two of the three hydrogen bonding groups. Accordingly, this approach structures an intermediary nucleobase to form just two hydrogen bonds with its complement, where the two hydrogen bonding groups that it forms are those to the hydrogen bonding groups that the non-standard nucleobase and a standard nucleobases share. For example (FIG. 5), 2-aminopurine can form two hydrogen bonds to both the non-standard dZ and to the standard dT. The dZ and dT hydrogen bonding patterns differ only in their hydrogen bonding group in the major groove, and 2-aminopurine does not present any hydrogen bonding group at all in this position. Likewise, 2-pyridone presents hydrogen bonding units to the hydrogen bonding elements that dP and diaminopurine have in common.

A fourth approach would exploit a chemically convertible intermediate nucleoside, one where the attached nucleobases is incorporated opposite the non-standard nucleobases. Then, a chemical step converts this nucleobase to a nucleobase that is Watson-Crick complementary to a non-standard nucleobase. For example, 2-amino-6-chloropurine (FIG. 6), who 2'-deoxynucleoside triphosphate is commercially available presents a hydrogen bond acceptor-acceptor-donor pattern to its complement; it is therefore incorporated by a DNA polymerase opposite dZ (pyDDA). Once incorporated, known procedures, incorporated herein by reference [Tan06][Mur91], convert it to either puADD (guanine, complementary to dC) or puDAD (diaminopurine, complementary to dT) by treatment with hydroxide or ammonia, respectively. Indeed, if the desire is to retain information about where the dZ was in the parent oligonucleotide, it can be treated with methanolic ammonium hydroxide with water present in an amount to create approximately equal amounts of guanine and diaminopurine.

Various of these strategies can be combined. For example, 6-chloropurine presents a puAA-hydrogen bonding pattern that is complementary to the "top" (nearest the major groove) hydrogen bonding units of dZ (or other implementations of the pyDDA hydrogen bonding pattern), and can be converted with ammonia into A, or with hydroxide into inosine, which is a complement to C. This has the net effect of converting a Z:P pair into either a C:G pair or a T:A pair in the products of successive polymerase copying, allowing these to be cloned. Further comparison of the products allows one to infer the position of the Z:P pair in the original oligonucleotide. The advantage of 6-chloropurine over 2-amino-6-chloropurine is that the first can be converted under milder conditions.

Given this process, one of ordinary skill in the art can recognize multiple architectures for assay that use nonstandard nucleotides and their orthogonality to detect natural oligonucleotides of specific sequence with extremely high signal-noise ratios. For example, an analyte can be amplified using PCR primers as normal designed to generate a particular product. As is well known in the art, to some extent, non-target DNA sequences will be amplified as well, it they are present in the complex biological mixture. If a capture sequence is introduced as a tag, these undesired amplicons will also be tagged. The invention is a process that comprises comprising contacting an oligonucleotide, which serves as a template, with a preselected primer under conditions where the primer and the template anneal to form a template-primer complex. This annealing is made possible by designing a primer sequences Watson-Crick complementary to portion of the template to be bound, following the expanded set of Watson-Crick pairing rules, described in the Figures. Is expanded Watson-Crick pairing roles exploit the size- and hydrogen bonding complementarity described in the art above. The remaining part of the template is single-stranded. For this reason, the primer can be extended by a DNA polymerase. Under normal extension conditions, extension occurs by matching a complementary nucleotide to a template nucleotide. This invention is based on the observation that under certain conditions, a nonstandard nucleotide is mismatched against a standard nucleotide, or a standard nucleotide is mismatched against a nonstandard nucleotide.

Thus, the second step in the invented process comprises incubating the template-primer complex with a polymerase in the presence of a mixture of one or more 2'-deoxynucleoside triphosphates, wherein the mixture comprises the triphosphate of a non-standard nucleoside. Here, the components of that mixture of triphosphate are chosen strategically to determine the structure of the product arising front primer extension. Here, if a product is sought where a pyrimidine nucleoside analog presenting a hydrogen bond donor-donor-acceptor hydrogen bonding pattern is incorporated opposite G in the template, that triphosphate mixture must include the triphosphate of that nucleoside analog, while excluding preferably dCTP, standard complement triphosphate to template G.

This process involves steps where single nucleotides are added by a polymerase the 3'-end of the annealed primer. The invention has four presently preferred implementations:

(a) The nucleotide being added comes from the triphosphate of a pyrimidine analog that presents the donor-donor-acceptor hydrogen bonding pattern, and is added by the polymerase to the primer under the direction of a guanine-containing nucleobase on the template.

(b) The nucleotide being added comes from 2'-deoxyguanosine triphosphate, and is added by the polymerase to the primer under the direction of nonstandard nucleotide in the templates that is a pyrimidine analog that presents a donor-donor-acceptor hydrogen bonding pattern.

(c) the nucleotide being added comes front the triphosphate of a purine analog that presents an acceptor-acceptor donor hydrogen bonding pattern, and is added by the polymerase to the primer under the direction of a cytosine-containing nucleobase on the template.

(d) The nucleotide being added comes from 2'-deoxycytidine triphosphate, and is added by the polymerase to the primer under the direction of q nonstandard purine nucleotide analog in the templates that that presents an acceptor-acceptor donor hydrogen bonding pattern.

The presently preferred processes (a) and (b) are most preferably done at a pH of 8 or greater, The presently preferred processes (c) and (d) are most preferably done at a pH of 7 or lower. The presently preferred process (a) is most preferably done in the absence of 2'-deoxycytidine triphosphate. The presently preferred process (c) is most preferably done in the absence of 2'-deoxyguanosine triphosphate.

LITERATURE

[Bro97] Brownie, J., Shawcross, S., Theaker, J. Whitcombe, D., Ferrie, R., Newton, C., Little, S. (1997). The elimination of primer-dimer accumulation in PCR. *Nucleic Acids Res.* 25, 3235-3241

[Elb04a] Elbeik, T., Markowitz, N., Nassos, P., Kumar, U., Beringer, S., Haller, B. and Ng, V. (2004) Simultaneous runs of the Bayer VERSANT HIV-1 version 3.0 and HCV bDNA version 3.0 quantitative assays on the system 340 platform provide reliable quantitation and improved work flow. *J. Clin. Microbiol.*, 42, 3120-3127.

[Elb04a] Elbeik, T., Surtihadi, J., Destree, M., Gorlin, J., Holodniy, M. Jortani, S.A., Kuramoto, K., Ng., V., Valdes, R., Valsamakis, A. et al. (2004) Multicenter evaluation of the performance characteristics of the Bayer VERSANT HVC RNA 3.0 assay (bDNA). *J. Clin. Microbiol.*, 42, 563-569.

[Hor95] Horlacher, J., Hottiger, M., Podust, V. N., Hübscher, U., Benner, S. A., (1995) Recognition by viral and cellular DNA polymerases of nucleosides bearing bases with non-standard hydrogen bonding patterns. *Proc. Natl. Acad. Sci.,* 92, 6329-6333

[Hut03] Hutter, D. and Benner, S. A. (2003) Expanding the genetic alphabet. Non-epimerizing nucleoside with the pyDDA hydrogen bonding pattern. *J. Org. Chem.* 68, 9839-9842

[Joh04] Johnson, S. C., Sherrill, C. B., Marshall, D. J., Moser, M. J., Prudent, J. R. (2004) A third base pair for the polymerase chain reaction: inserting isoC and isoG. *Nucleic Acids Res.* 32, 1937-1941

[Jur00] Jurczyk, S. C., Horlacher, J., Devine, K. G., Benner, S. A. Battersby, T. R. (2000) Synthesis and characterization of oligonucleotides containing 2'-deoxyxanthosine using phosphoramidite chemistry. *Helv. Chim. Acta* 83, 1517-1524

[Jur98] Jurczyk, S., Kodra, J. T., Rozzell, J. D., Jr., Benner, S. A., Battersby, T. R. (1998) Synthesis of oligonucleotides containing 2'-deoxyisoguanosine and 2'-deoxy-5-methyliso-cytidine using phosphoramidite chemistry. *Helv. Chim. Acta* 81, 793-811]

[Jur99] Jurczyk, S. C., Battersby, Kodra, J. T., Park, J.-H., Benner, S. A. (1999) Synthesis of 2'-deoxyisoguanosine triphosphate and 2'-deoxy-5-methyl-isocytidine triphosphate, *Helv. Chim. Acta.* 82, 1005-1015

[Kim09] Kim, H. J., Leal, N. A., Benner, S. A. (2009) 2'-Deoxy-1-methylpseudocytidine, a stable analog of 2'-deoxy-5-methylisocytidine. *Bioorg Med. Chem.* 17, 3728-373

[Kod97] Kodra, J., Benner, S. A. (1997) Synthesis of an N-alkyl derivative of 2'-deoxyisoguanosine. *Syn. Lett.*, 939-940

[Lut99] Lutz, S., Burgstaller, P., Benner, S. A. (1999) An in vitro screening technique for polymerases that can incorporate modified nucleotides. Pseudouridine as a substrate for thermostable polymerases. *Nucl. Acids Res.* 27, 2792-2798]

[Mar04] Martinot, T. A., Benner, S. A. (2004) Expanding the genetic alphabet: 7-Deaza-isoguanosine favors the 1N-H keto form by $10^3$-to-1 over the enol. *J. Org. Chem.* 69, 3972-3975

[Mur91] Murakami, K., Shirasaka, T., Yoshioka, H., Kojima, E., Aoki, S., Ford, Jr. H., Driscoll, J. S., Kelley, J. A., Mitsuya, H. (1991) *Escherichia coli* mediated biosynthesis and in vitro Anti-HIV Activity of lipophilic 6-Halo-2',3'-dideoxypurine nucleosides. *J. Med. Chem.*, 34, 1606-1612

[Pic90] Piccirilli, J. A., Krauch, T., Moroney, S. E., Benner, S. A. (1990) Extending the genetic alphabet. Enzymatic incorporation of a new base pair into DNA and RNA. *Nature* 343, 33-37

[Pic91] Piccirilli, J. A., Krauch, T., MacPherson, L. J., Benner, S. A. (1991) A direct route to 3-(ribofuranosyl)-pyridine nucleosides. *Helv. Chim. Acta* 74, 397-406

[Sep76] Sepiol, J., Kazimierczuk, Z., Shugar, D. Z. (1976) Tautomerism of iso-guanosine and solvent-induced keto-enol equilibrium. *Z. Naturforsch* 31C, 361-370

[Sis05] Sismour, A. M., Benner, S. A. (2005) The use of thymidine analogs to improve the replication of an extra DNA base pair: A synthetic biological system, *Nucl. Acids Res.* 33, 5640-5646

[Swi89] Switzer C. Y., Moroney, S. E., Benner, S. A. (1989) Enzymatic incorporation of a new base pair into DNA and RNA. *J. Am. Chem. Soc.* 111, 8322-8323

[Swi93] Switzer C. Y., Moroney, S. E., Benner, S. A. (1993) Enzymatic recognition of the base pair between iso-cytidine and iso-guanosine. *Biochemistry* 32, 10489-10496

[Tan06] Tang, Y., Ramaiah, M., Vince, R. (2006) Synthesis and biological evaluation of carboacyclic nucleosides with (Z) and (E)-9-[4,4-bis(hydroxymethyl)]-2-butenyl side chain. *Bioorg. Med. Chem. Lett.* 14, 5866-5875

[Voe93] Voegel, J. J., von Krosigk, U., Benner, S. A, (1993) Synthesis and tautomeric equilibrium of 6-amino-5-benzyl-3-methylpyrazin-2-one. An acceptor-donor-donor nucleoside base analog. *J. Org. Chem.* 58, 7542-7547

[Voe96a] Voegel, J. J., Benner, S. A. (1996) Synthesis and characterization of non-standard nucleosides and nucleotides bearing the acceptor-donor-donor pyrimidine analog 6-amino-3-methylpyrazin-2-one. *Helv. Chim. Acta* 79, 1863-1880

[Voe96b] Voegel, J. J., Benner, S. A. (1996) Synthesis, molecular recognition & enzymology of oligonucleotides containing the non-standard base pair between 5-aza-7-deaza-iso-guanine 6-amino-3-methylpyrazin-2-one, a donor-acceptor-acceptor purine analog and an acceptor-donor-donor pyrimidine analog. *Helv. Chim. Acta* 79, 1881-1898

[Von95b] von Krosigk, U., Benner, S. A. (1995) pH-independent triple helix formation by an oligonucleotide containing a pyrazine donor-donor-acceptor base. *J. Am. Chem. Soc.* 117, 5361-5362

[Yan06] Yang, Z., Hutter, D., Sheng, P., Sismour, A. M. and Benner, S. A. (2006) Artificially expanded genetic information system. A new base pair with an alternative hydrogen bonding pattern. *Nucleic Acids Res.,* 34, 6095-6101.

[Yan07] Yang, Z., Sismour, A. M., Sheng, P., Puskar, N. L., Benner, S. A. (2007) Enzymatic incorporation of a third nucleobase pair. *Nucl. Acids Res.* 35, 4238-4249

EXAMPLE

Example 1

Incorporating dZ into oligonucleotides opposite dG via primer extension using Therminator™ DNA polymerase.

Summary of the Results

The dZ containing oligo can be efficiently generated through primer extension using standard template and THERMINATOR™ DNA polymerase. These data are shown in FIG. 7 and FIG. 8.

Oligonucleotides Used in this Example

Oligonuleatides for glyceraldehyde-3-phosphate
dehydrogenase (GAP)
Lua3-Std24-Biot:
                                       SEQ. ID. NO. 1
3'-CTA ACA TTC TAA ACT ATT TCA CAT--Biot-5'

SEQ. ID. NO. 2
3'-CTA ACA TTC TAA ACT ATT TCA CAT-GGACTGGACGGCAGA

TCTTTT-Biot-5'

GAP-prim-21-Biot:
                                       SEQ. ID. NO. 3
3'-ZTA AZA TTZ TAA AZT ATT TZA ZAT-GGACTGGACGGCAGA TCTTTT-Biot-5'

GAP-F-Std45:
                                       SEQ. ID. NO. 4
5'-GAT TGT AAG ATT TGA TAA AGT GTACCTGACCTGCCGTCTA

GAAAA-3'

GAP-prim-21-Biot:
                                       SEQ. ID. NO. 5
3'-CTA AZA TTZ TAA AZT ATT TZA ZAT-GGACTGGACGGCAGA TCTTTT-Biot-5'

SEQ. ID. NO. 6
5'-GAT TPT AAP ATT TPA TAA APT PTACCTGACCTGCCGTCTA

GAAAA-3'

Oligonucleotides for topoisomerase (TOP)
Lua10-Std24-Biot:
                                       SEQ. ID. NO. 7
3'-ACA TCT AAA CAT ACA TAC ATA CTA-Biot-5'

SEQ. ID. NO. 8
3'-ACA TCT AAA CAT ACA TAC ATA CTA-CTGTCGGGGCCTACT

CTTG-Biot-5'

TOP-prim-19-Biot:
                                       SEQ. ID. NO. 9
3'-AZA TZT AAA ZAT AZA TAZ ATA ZTA-CTGTCGGGGCCTACT CTTG-Biot-5'

Top-F-Std43:
                                       SEQ. ID. NO. 10
5'-TGT AGA TTT GTA TGT ATG TAT GAT GACAGCCCGGATGA

GAAC-3'

TOP-prim-19-Biot:
                                       SEQ. ID. NO. 11
3'-ACA TZT AAA ZAT AZA TAZ ATA ZTA-CTGTCGGGGCCTACT CTTG-Biot-5'

SEQ. ID. NO. 12
5'-TGT APA TTT PTA TPT ATP TAT PAT GACAGCCCGGATGA

GAAC-3'

Oligonucleotides for human epidermal growth factor
(HBE)
Lua14-Std24-Biot:
                                       SEQ. ID. NO. 13
3'-TTT CAT ATC ATT CTA CAT ATC ATC-Biot-5'

SEQ. ID. NO. 14
3'-TTT CAT ATC ATT CTA CAT ATC ATC-CGGGGTCAACGGCAG

ATCCT-Biot-5'

HBE-prim-20-Biot:
                                       SEQ. ID. NO. 15
3'-TTT ZAT ATZ ATT ZTA ZAT ATZ AT-CGGGGTCAACGGCAGA TCCT-Biot-5'

HBE-F-Std43:
                                       SEQ. ID. NO. 16
5'-AAA GTA TAG TAA GAT GTA TAG TA GCCCCAGTTGCCGTCT

AGGA-3'

HBE-prim-20-Biot:
                                       SEQ. ID. NO. 15
3'-TTT ZAT ATZ ATT ATZ ZAT ATZ AT-CGGGGTCAACGGCAGA TCCT-Biot-5'

HBE-F-43-5P:
                                       SEQ. ID. NO. 17
5'-AAA PTA TAP TAA PAT PTA TAP TA GCCCCAGTTGCCGTCT

AGGA-3'

Oligonucleotides for the Myc gene (MYC)
Lua19-Std24-Biot:
                                       SEQ. ID. NO. 18
3'-CAT AAA CTC ATT CAT TAA CTA ACT-Biot-5'

SEQ. ID. NO. 19
3'-CAT AAA CTC ATT CAT TAA CTA ACT-AGGAGGAATACGGAG

ATAGTA-Biot-5'

MYC-prim-21-Biot:
                                       SEQ. ID. NO. 20
3'-ZAT AAA ZTZ ATT ZAT TAA ZTA AZT-AGGAGGAATACGGAG ATAGTA-Biot-5'

MYC-F-Std45:
                                       SEQ. ID. NO. 21
5'-GTA TTT GAG TAA GTA ATT GAT TGA TCCTCCTTATGCCTC

TATCAT-3'

MYC-prim-21-Biot:
                                       SEQ. ID. NO. 22
3'-CAT AAA ZTZ ATT ZAT TAA ZTA AZT-AGGAGGAATACGGAG ATAGTA-Biot-5'

MYC-F-45-5P:
                                       SEQ. ID. NO. 23
5'-GTA TTT PAP TAA PTA ATT PAT TPA TCCTCCTTATGCCTC

TATCAT-3'

Protocol for the Primer Extension

| | 1 | 2 | 3 | 4 | 5 |
|---|---|---|---|---|---|
| γ-$^{32}$P-Primer (1 μM) | 0.1 μL | 0.1 μL | 0.1 μL | 0.1 μL | 0.1 μL |
| Biotin-Primer (1 μM) | 2 μL | 2 μL | 2 μL | 2 μL | 2 μL |
| Template (2 μM) | 1.5 μL Std-Temp | 1.5 μL Std-Temp | 1.5 μL Std-Temp | 1.5 μL dP-Temp | 1.5 μL dP-Temp |
| 10x Thermopol Buffer (pH 9.0)) | 1 μL | 1 μL | 1 μL | 1 μL | 1 μL |

-continued

|  | 1 | 2 | 3 | 4 | 5 |
| --- | --- | --- | --- | --- | --- |
| dNTP (1 mM) | 1 μL dA, T, G/TP | 1 μL dNTP | 1 μL dA, T, G, Z/TP | 1 μL dNTP | 1 μL dNTP + dZTP |
| DNA polymerase (1 U/μL) | 1 μL Therminator | 1 μL Therminator | 1 μL Therminator | 1 μL Taq | 1 μL Taq |
| H₂O (final volume of 10 μl) | 3.5 μL | 3.5 μL | 3.5 μL | 3.5 μL | 3.5 μL |

Note:
1 (negative control): Therminator, dATP + dTTP + dGTP; 2 (positive control): Therminator, dATP) + dTTP + dGTP + dCTP; 3 (experiment): Therminator, dATP + dTTP + dGTP + dZTP; 4 (negative control): Taq, dNTP; 5 (experiment); Taq, DNTP + dZTP.

Primer Extension with $^{32}$P-Labeled Primer

5'-$^{32}$P-Labeled primer (0.1 pmole plus cold primer (biotin-primer) 2 pmole, final assay concentration 210 nM) was annealed to either standard template or dP containing template (3 pmole, final assay concentration 300 nM) in thermpol reaction buffer by heating (5 min 95° C.) and then slow cooling (0.5 h) to room temperature. dNTP and DNA polymerase were added at room temperature, followed by incubating at 72° C. for 1 min or 5 min, and then quenched by dilution into PAGE loading/quench buffer (8 μL, 10 mM EDTA in formamide). Samples were resolved by electrophoresis using a 16% PAGE (7 M urea). The gel was analyzed using MolecularImager software.

Primer Extension without $^{32}$P-Labeled Primer

Biotin-labeled primer (2 pmole, final assay concentration 210 nM) was annealed to either standard template or dP containing template (3 pmole, final assay concentration 300 nM) in thermpol reaction buffer by heating (5 min 95° C.) and then slow cooling (0.5 h) to room temperature. The biotin-labeled primer extended under three different conditions: 2 (positive control): Therminator, dNTP; 3 (experiment): Therminator, dATP+dTTP+dGTP+dZTP; 5 (experiment): Taq, dNTP+dZTP, dNTP and DNA polymerase were added at room temperature, followed by incubating at 72° C. for 5 min. The reaction was quenched with 2 μL of 20 mM EDTA, and diluted with 190 μL of ddH₂O to give the fully extended full-length dZ containing or control oligonucleotide (final concentration 10 fmoles/μL).

1 (negative control): Therminator, dATP+dTTP+dGTP; 2 (positive control): Therminator, dATP+dTTP+dGTP+dCTP; 3 (experiment): Therminator, dATP+dTTP+dGTP+dZTP; 4 (negative control): Taq, dNTP; 5 (experiment): Taq, dNTP+dZTP.

What is claimed is:

1. A process comprising (a) contacting an oligonucleotide template with a preselected primer under conditions where said primer and said template anneal to form a template-primer complex, (b) incubating said complex with a polymerase in the presence of the triphosphate of a non-standard nucleoside, wherein (c) said polymerase catalyzes the addition to the 3'-end of said primer of a non-standard nucleoside derived from said triphosphate opposite a standard nucleotide in said template, wherein the nucleobase of said non-standard nucleoside triphosphate is

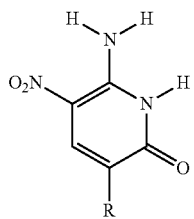

wherein R is the point of attachment of said nucleobase to said nucleoside triphosphate, and wherein the nucleobase of said standard nucleotide is guanine.

2. The process of claim 1, where said incubation is done at a pH of 8 or higher.

3. The process of claim 1, where said incubation is done in the absence of 2'-deoxycytidine triphosphate.

4. The process of claim 1, where said polymerase is Therminator.

5. A process comprising (a) contacting an oligonucleotide template with a preselected primer under conditions where said primer and said template anneal to form a template-primer complex, (b) incubating said complex with a polymerase in the presence of a triphosphate of a standard nucleoside, wherein (c) said polymerase catalyzes the addition to the 3'-end of said primer of a standard nucleoside derived from said triphosphate opposite a non-standard nucleotide in said template, wherein the nucleobase of said standard nucleoside triphosphate is guanine, and the nucleobase of said non-standard template nucleotide is

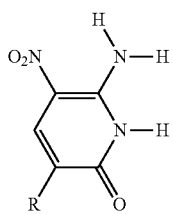

wherein R is the point of attachment of said nucleobase to the template.

6. The process of claim 5, where said incubation is done at a pH of 8 or higher.

7. The process of claim 5, where said polymerase is Therminator.

8. A process comprising (a) contacting an oligonucleotide template with a preselected primer under conditions where said primer and said template anneal to form a template-primer complex, (b) incubating said complex with a polymerase in the presence of a triphosphate of a non-standard nucleoside, wherein (c) said polymerase catalyzes the addition to the 3'-end of said primer of a non-standard nucleoside derived from said triphosphate opposite a standard nucleotide in said template, wherein the nucleobase of said non-standard nucleoside triphosphate is

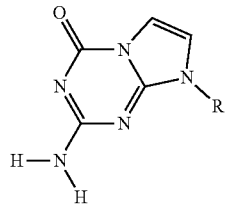

wherein R is the point of attachment of said nucleobase to said nucleoside triphosphate, and wherein the nucleobase of said standard nucleotide is cytosine.

9. The process of claim 8, where said incubation is done at a pH of 7 or lower.

10. The process of claim 8, where said incubation is done in the absence of 2'-guanosine triphosphate.

11. The process of claim 8, where said polymerase is Therminator.

12. A process comprising (a) contacting an oligonucleotide template with a preselected primer under conditions where said primer and said template anneal to form a template-primer complex, (b) incubating said complex with a polymerase in the presence of a triphosphate of a standard nucleoside, wherein (c) said polymerase catalyzes the addition to the 3'-end or said primer of a standard nucleoside derived from said triphosphate opposite a non-standard nucleotide in said template, wherein the nucleobase of said standard nucleoside triphosphate is cytosine, and the nucleobase of said non-standard template nucleotide is

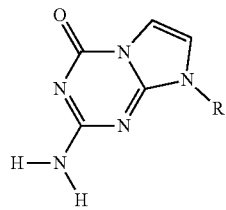

wherein R is the point of attachment of said nucleobase to the template.

13. The process of claim 8, where said incubation is done at a pH of 7 or higher.

14. The process of claim 8, where said polymerase is Therminator.

\* \* \* \* \*

SEQUENCE LISTING

```
<160> NUMBER OF SEQ ID NOS: 23

<210> SEQ ID NO 1
<211> LENGTH: 43
<212> TYPE: DNA
<213> ORGANISM: Artificial Sequence
<220> FEATURE:
<223> OTHER INFORMATION: synthetic

<400> SEQUENCE: 1
aaagtatagt aagatgtata gtagccccag ttgccgtcta gga          43

<210> SEQ ID NO 2
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (4)..(4)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (9)..(9)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (13)..(13)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (16)..(16)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (21)..(21)
<223> OTHER INFORMATION: 7-amino-9-(1'-beta-D-2'-deoxyribofuranosyl)-
      imidazo[1,2-c]pyrimidin-5(1H)-one

<400> SEQUENCE: 2
```
aaantatant aanatntata ntagccccag ttgccgtcta gga         43

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
atcatacata catacaaatc taca         24

<210> SEQ ID NO 4
<211> LENGTH: 45
<212> TYPE: DNA
<213> ORGANISM: Artificial Sequence
<220> FEATURE:
<223> OTHER INFORMATION: synthetic

<400> SEQUENCE: 4
atgatagagg cataaggagg atcaatcaat tacttactca aatac         45

<210> SEQ ID NO 5
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (27)..(27)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (33)..(33)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one

<400> SEQUENCE: 5
atgatagagg cataaggagg atnaatnaat tanttantna aatac         45

<210> SEQ ID NO 6
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (27)..(27)

```
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (33)..(33)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (45)..(45)
<223> OTHER INFORMATION: 6-amino-3-(2'-deoxy)-D-ribofuranosyl)-5-nitro-
      1H-pyridin-2-one

<400> SEQUENCE: 6
atgatagagg cataaggagg atnaatnaat tanttantna aatan              45

<210> SEQ ID NO 7
<211> LENGTH: 24
<212> TYPE: DNA
<213> ORGANISM: Artificial Sequence
<220> FEATURE:
<223> OTHER INFORMATION: synthetic

<400> SEQUENCE: 7
ctactataca tcttactata cttt                                      24

<210> SEQ ID NO 8
<211> LENGTH: 45
<212> TYPE: DNA
<213> ORGANISM: Artificial Sequence
<220> FEATURE:
<223> OTHER INFORMATION: synthetic

<400> SEQUENCE: 8
gattgtaaga tttgataaag tgtacctgac ctgccgtcta gaaaa               45

<210> SEQ ID NO 9
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (9)..(9)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (14)..(14)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (20)..(20)
<223> OTHER INFORMATION: 7-amino-9-(1'-beta-D-2'-deoxyribofuranosyl)-
      imidazo[1,2-c]pyrimidin-5(1H)-one
<220> FEATURE:
```

```
<221> NAME/KEY: misc_feature
<222> LOCATION: (22)..(22)
<223> OTHER INFORMATION: 7-amino-9-(1'-beta-D-2'-deoxyribofuranosyl)-
      imidazo[1,2-c]pyrimidin-5(1H)-one

<400> SEQUENCE: 9
gattntaana tttnataaan tntacctgac ctgccgtcta gaaaa              45

<210> SEQ ID NO 10
<211> LENGTH: 45
<212> TYPE: DNA
<213> ORGANISM: Artificial Sequence
<220> FEATURE:
<223> OTHER INFORMATION: synthetic

<400> SEQUENCE: 10
gtatttgagt aagtaattga ttgatcctcc ttatgcctct atcat              45

<210> SEQ ID NO 11
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (7)..(7)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (9)..(9)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (13)..(13)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (19)..(19)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (23)..(23)
<223> OTHER INFORMATION: 7-amino-9-(1'-beta-D-2'-deoxyribofuranosyl)-
      imidazo[1,2-c]pyrimidin-5(1H)-one

<400> SEQUENCE: 11
gtatttnant aantaattna ttnatcctcc ttatgcctct atcat              45

<210> SEQ ID NO 12
<211> LENGTH: 43
<212> TYPE: DNA
<213> ORGANISM: Artificial Sequence
<220> FEATURE:
<223> OTHER INFORMATION: synthetic

<400> SEQUENCE: 12
gttctcatcc ggggctgtca tcatacatac atacaaatct aca               43

<210> SEQ ID NO 13
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
```

```
<222> LOCATION: (22)..(22)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (30)..(30)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (34)..(34)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one

<400> SEQUENCE: 13
gttctcatcc ggggctgtca tnatanatan atanaaatnt aca           43

<210> SEQ ID NO 14
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (22)..(22)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (30)..(30)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (34)..(34)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (39)..(39)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (42)..(42)
<223> OTHER INFORMATION: 6-amino-3-(2'-deoxy)-D-ribofuranosyl)-5-nitro-
      1H-pyridin-2-one

<400> SEQUENCE: 14
gttctcatcc ggggctgtca tnatanatan atanaaatnt ana           43

<210> SEQ ID NO 15
<211> LENGTH: 24
<212> TYPE: DNA
<213> ORGANISM: Artificial Sequence
<220> FEATURE:
<223> OTHER INFORMATION: synthetic

<400> SEQUENCE: 15
```
tacactttat caaatcttac aatc                                          24

<210> SEQ ID NO 16
<211> LENGTH: 24
<212> TYPE: DNA
<213> ORGANISM: Artificial Sequence
<220> FEATURE:
<223> OTHER INFORMATION: synthetic

<400> SEQUENCE: 16
tcaatcaatt acttactcaa atac                                          24

<210> SEQ ID NO 17
<211> LENGTH: 44
<212> TYPE: DNA
<213> ORGANISM: Artificial Sequence
<220> FEATURE:
<223> OTHER INFORMATION: synthetic

<400> SEQUENCE: 17
tcctagacgg caactggggc ctactataca tcttactata cttt                    44

<210> SEQ ID NO 18
<211> LENGTH: 43
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (23)..(23)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (28)..(28)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (31)..(31)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (35)..(35)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (40)..(40)
<223> OTHER INFORMATION: 6-amino-3-(2'-deoxy)-D-ribofuranosyl)-5-nitro-
      1H-pyridin-2-one

<400> SEQUENCE: 18
tcctagacgg caactggggc tantatanat nttantatan ttt                     43

<210> SEQ ID NO 19
<211> LENGTH: 43
<212> TYPE: DNA
<213> ORGANISM: Artificial Sequence
<220> FEATURE:
<223> OTHER INFORMATION: synthetic

<400> SEQUENCE: 19
tgtagatttg tatgtatgta tgatgacagc cccggatgag aac                     43

<210> SEQ ID NO 20
<211> LENGTH: 43

```
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (5)..(5)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (10)..(10)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (14)..(14)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (18)..(18)
<223> OTHER INFORMATION: 7-amino-9-(1'-beta-D-2'-deoxyribofuranosyl)-
      imidazo[1,2-c]pyrimidin-5(1H)-one
<220> FEATURE:
<221> NAME/KEY: misc_feature
<222> LOCATION: (22)..(22)
<223> OTHER INFORMATION: 7-amino-9-(1'-beta-D-2'-deoxyribofuranosyl)-
      imidazo[1,2-c]pyrimidin-5(1H)-one

<400> SEQUENCE: 20
tgtanatttn tatntatnta tnatgacagc cccggatgag aac                    43

<210> SEQ ID NO 21
<211> LENGTH: 45
<212> TYPE: DNA
<213> ORGANISM: Artificial Sequence
<220> FEATURE:
<223> OTHER INFORMATION: synthetic

<400> SEQUENCE: 21
ttttctagac ggcaggtcag gtacacttta tcaaatctta caatc                  45

<210> SEQ ID NO 22
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (32)..(32)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (41)..(41)
<223> OTHER INFORMATION: 6-amino-3-(2'-deoxy)-D-ribofuranosyl)-5-nitro-
      1H-pyridin-2-one
```

```
<400> SEQUENCE: 22
ttttctagac ggcaggtcag gtananttta tnaaatntta naatc                45

<210> SEQ ID NO 23
<211> LENGTH: 45
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (24)..(24)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (26)..(26)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (32)..(32)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (37)..(37)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (41)..(41)
<223> OTHER INFORMATION: 6-amino-3-(2'-deoxy)-D-ribofuranosyl)-5-nitro-
      1H-pyridin-2-one
<220> FEATURE:
<221> NAME/KEY: misc_feature
<222> LOCATION: (45)..(45)
<223> OTHER INFORMATION: 6-amino-3-(2'-deoxy)-D-ribofuranosyl)-5-nitro-
      1H-pyridin-2-one

<400> SEQUENCE: 23
ttttctagac ggcaggtcag gtananttta tnaaatntta naatn                45
```